(12) United States Patent
Carry et al.

(10) Patent No.: US 6,420,566 B2
(45) Date of Patent: Jul. 16, 2002

(54) PHARMACEUTICAL COMPOSITIONS CONTAINING A 4, 5-DIHYDRO-1, 3-THIAZOL-2-YLAMINE DERIVATIVE, NOVEL DERIVATIVES AND PREPARATION THEREOF

(75) Inventors: Jean-Christophe Carry, Saint Maur des Fosses; Dominique Damour, Orly; Claude Guyon, Saint Maur des Fosses; Serge Mignani, Chatenay-Malabry; Eric Bacque, Morsang sur Orge; Antony Bigot, Massy, all of (FR)

(73) Assignee: Aventis Pharma S.A., Antony Cedex (FR)

( * ) Notice: Subject to any disclaimer, the term of this patent is extended or adjusted under 35 U.S.C. 154(b) by 0 days.

(21) Appl. No.: 09/878,045

(22) Filed: Jun. 8, 2001

Related U.S. Application Data

(60) Provisional application No. 60/231,613, filed on Sep. 11, 2000.

(30) Foreign Application Priority Data

Jun. 9, 2000 (FR) .............................................. 00 07396

(51) Int. Cl.⁷ ..................... C07D 277/08; A61K 31/426
(52) U.S. Cl. ..................................................... 548/184
(58) Field of Search .......................... 548/184; 514/369

(56) References Cited

U.S. PATENT DOCUMENTS

| 4,695,639 A | * | 9/1987 | Takanohashi et al. | ........ 548/165 |
| 5,089,512 A | * | 2/1992 | Wilson et al. | .............. 514/365 |
| 6,001,855 A | * | 12/1999 | Alig et al. | .................. 514/326 |

FOREIGN PATENT DOCUMENTS

| WO | 9412165 | 6/1994 |
| WO | 9511231 | 4/1995 |
| WO | 9614842 | 5/1996 |

* cited by examiner

Primary Examiner—Joseph K. McKane
Assistant Examiner—Golam M. M. Shameem
(74) Attorney, Agent, or Firm—Balaram Gupta

(57) ABSTRACT

The present invention relates to pharmaceutical compositions containing, as active principle, a 4,5-dihydro-1,3-thiazol-2-ylamine derivative of formula (I):

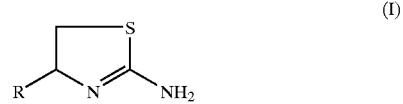

in which R represents an -alk-S-alk-Ar radical, a phenyl radical or a phenyl radical substituted with alkoxy or halogen, or to one of the pharmaceutically acceptable salts thereof, to the novel derivatives of formula (I) and to their preparation.

22 Claims, No Drawings

PHARMACEUTICAL COMPOSITIONS CONTAINING A 4, 5-DIHYDRO-1, 3-THIAZOL-2-YLAMINE DERIVATIVE, NOVEL DERIVATIVES AND PREPARATION THEREOF

This application claims the benefit of U.S. Provisional Application No. 60/231,613, filed Sep. 11, 2000, which claims the benefit of priority of French Patent Application No. 00/07,396, filed Jun. 09, 2000.

The present invention relates to pharmaceutical compositions containing, as active principle, a 4,5-dihydro-1,3-thiazol-2-ylamine derivative of formula (I):

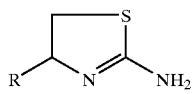

or to one of the pharmaceutically acceptable salts thereof, to the novel derivatives of formula (I) and to their preparation.

The compounds of formula (I) are inhibitors of nitric oxide synthase and particularly of the inducible isoform of this enzyme.

Nitric oxide (NO) is a diffusable radical involved in many physiological and pathological processes. It is synthesized by oxidation of L-arginine, this reaction being catalyzed by a family of enzymes known as nitric oxide synthases or NO-synthases (NOSs), which is referenced in the international enzyme nomenclature system under the number E.C. 1.14.13.39.

Three NOS isoforms, two of which are constitutive and one inducible, are known:

- a neuronal NOS (NOS-1 or nNOS) was originally isolated and cloned from nerve tissue in which it is a constitutive enzyme. NOS-1 produces NO in response to various physiological stimuli such as the activation of membrane receptors according to a mechanism dependent on calcium and on calmodulin;
- an inducible NOS (NOS-2 or iNOS) can be induced in response to immunological stimuli such as, for example, cytokines or bacterial antigens in various cells such as, for example, macrophages, endothelial cells, hepatocytes, glial cells, as well as many other types of cell. The activity of this isoform is not regulated by calcium. Consequently, once induced, it produces large amounts of NO over prolonged periods.
- an endothelial NOS (NOS-3 or eNOS) is constitutive and calcium/calmodulin-dependent. It was originally identified in vascular endothelial cells, in which it generates NO in response to physiological stimuli such as the activation of membrane receptors.

The NO produced by the neuronal and endothelial constitutive isoforms (NOS-1 and NOS-3) is generally involved in intercellular signalling functions. For example, the endothelial cells which line the inner wall of the blood vessels induce the relaxation of the underlying smooth muscle cells via the production of NO. It thus contributes towards regulating the arterial pressure.

The NO produced in large amount by the inducible isoform NOS-2 is, inter alia, involved in pathological phenomena associated with acute and chronic inflammatory processes in a large variety of tissues and organs.

An excessive production of NO by induction of NOS-2 thus plays a part in degenerative pathologies of the nervous system such as, for example, multiple sclerosis, cerebral, focal or global ischemia, cerebral or spinal trauma, Parkinson's disease, Huntington's disease, Alzheimer's disease, amyotrophic lateral sclerosis, migraine, depression, schizophrenia, anxiety and epilepsy. Similarly, aside from the central nervous system, the induction of NOS-2 is involved in numerous pathologies with inflammatory components, such as, for example, diabetes, atherosclerosis, myocarditis, arthritis, arthrosis, asthma, irritable bowel syndrome, Crohn's disease, peritonitis, gastro-esophageal reflux, uveitis, Guillain-Barré syndrome, glomerulonephritis, lupus erythematosus and psoriasis. NOS-2 has also been implicated in the growth of certain forms of tumors such as, for example, epitheliomas, adenocarcinomas or sarcomas, and in infections with Gram-positive or Gram-negative intracellular or extracellular bacteria.

In all the situations in which an overproduction of NO is deleterious, it thus appears to be desirable to reduce the production of NO by administering substances capable of inhibiting NOS-2.

Thiazoline-based NOS inhibitors are described in particular in patent applications WO 94/12165, WO95/11231 and WO 96/14842.

The pharmaceutical compositions according to the present invention are those containing, as active principle, a derivative of formula (I) in which R represents an -alk-S-alk-Ar radical, a phenyl radical or a phenyl radical substituted with alkoxy or halogen, Ar is a phenyl radical and alk represents an alkylene radical.

When R is a substituted phenyl it is preferably monosubstituted, and in particular in position 3 or 4.

In the preceding definitions and in those which follow, the alkyl, alkylene and alkoxy radicals and the alkyl and alkoxy portions contain 1 to 6 carbon atoms in a straight or branched chain.

The halogen atoms are bromine, chlorine, iodine and fluorine atoms, and more particularly the bromine atom.

The alkoxy radicals are, in particular, methoxy, ethoxy and propoxy radicals, and more preferably methoxy radicals R preferably represents a phenyl radical, a phenyl radical which is monosubstituted with alkoxy and more particularly with methoxy or a halogen atom and more particularly with a bromine atom.

The compounds of formula (I) contain one or more asymmetric carbon atoms and can thus be in racemic form or in the form of enantiomers and diastereoisomers; these also form part of the invention, as well as mixtures thereof.

Moreover, the compounds of formula (I) can be in the tautomeric form (Ia):

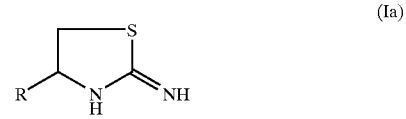

These tautomers also form part of the invention.

The preferred pharmaceutical compositions are those containing a compound of formula (I), the racemic mixture, enantiomers and diastereoisomers thereof, the tautomer thereof and the pharmaceutically acceptable salts thereof chosen from the following compounds: 4-(3-bromophenyl)-4,5-dihydro-1,3-thiazol-2-ylamine 4-(4-methoxyphenyl)-4,5-dihydro-1,3-thiazol-2-ylamine 4-phenyl-4,5-dihydro-1,3-thiazol-2-ylamine 4-(benzylsulfanylmethyl)-4,5-dihydro-1,3-thiazol-2-ylamine.

The pharmaceutical compositions that are even more preferred are those containing, as active principle, a compound of formula (I), the tautomer thereof or pharmaceutically acceptable salts thereof, chosen from the following compounds:

(4RS)-4-(3-bromophenyl)-4,5-dihydro-1,3-thiazol-2-ylamine
4-(4-methoxyphenyl)-4,5-dihydro-1,3-thiazol-2-ylamine
(−)-(4R)-4-(4-methoxyphenyl)-4,5-dihydro-1,3-thiazol-2-ylamine
(−)-(4R)-4-phenyl-4,5-dihydro-1,3-thiazol-2-ylamine.

The derivative of formula (I) for which R is phenyl is known (Chem. Abst., registry Number 76999-87-6).

The other derivatives of formula (I) are novel and as such form part of the invention.

The compounds of formula (I) that are preferred are the following compounds:

4-(3-bromophenyl)-4,5-dihydro-1,3-thiazol-2-ylamine
4-(4-methoxyphenyl)-4,5-dihydro-1,3-thiazol-2-ylamine
4-(benzylsulfanylmethyl)-4,5-dihydro-1,3-thiazol-2-ylamine the racemic mixtures, enantiomers, diastereoisomers and mixtures thereof, the tautomers thereof and the pharmaceutically acceptable salts thereof.

The compounds that are even more preferred are the following:

(4RS)-4-(3-bromophenyl)-4,5-dihydro-1,3-thiazol-2-ylamine
4-(4-methoxyphenyl)-4,5-dihydro-1,3-thiazol-2-ylamine
(−)-(4R)-4-(4-methoxyphenyl)-4,5-dihydro-1,3-thiazol-2-ylamine the tautomers thereof and the pharmaceutically acceptable salts thereof.

The compounds of formula (I) can be prepared by cyclization of a derivative of formula:

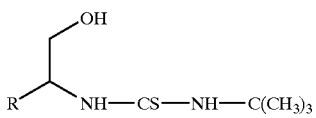

(II)

in which R has the same meanings as in formula (I).

This cyclization is generally carried out using an acid such as hydrochloric acid, in aqueous medium, at a temperature of 100° C. 6N hydrochloric acid is preferably used.

The derivatives of formula (II) can be obtained according to the reaction scheme below:

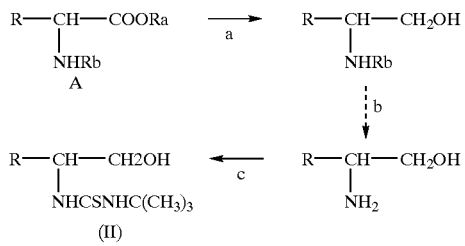

In these formulae, R has the same meanings as in formula (I), Ra represents a hydrogen atom or an alkyl or alkoxycarbonyl radical, preferably methyl, ethyl or isobutyloxycarbonyl, and Rb is a hydrogen atom or a protecting group for the amine function such as those described by T. W. Greene, Protective groups in Organic Synthesis, J. Wiley-Interscience Publication (1991), and preferably an acetyl or tert-butoxycarbonyl radical.

The reduction step a is preferably carried out using a hydride such as sodium borohydride or lithium aluminum hydride, in a (1–4C) aliphatic alcohol or tetrahydrofuran, at a temperature of between 10° C. and 30° C., or alternatively using a borane derivative such as the BH$_3$-THF complex, in a solvent such as tetrahydrofuran, at a temperature of between 0° C. and 30° C.

The deprotection reaction b for the compounds for which Rb is a protecting group for the amine function is carried out by any deprotection method known to those skilled in the art, and in particular those described by T. W. Greene, Protective groups in Organic Synthesis, J. Wiley-Interscience Publication (1991). When the protecting group is an acetyl radical, this reaction is preferably carried out using aqueous hydrochloric acid, at a temperature of 100° C. When the protecting group is a tert-butoxycarbonyl radical, this reaction is carried out using hydrochloric acid in dioxane, at a temperature in the region of 20° C.

Reaction c is carried out by the action of tert-butyl isothiocyanate, in an inert solvent such as a (1–4C) aliphatic alcohol (preferably methanol or ethanol), in the presence of a tertiary amine such as triethylamine, at a temperature of between 20° C. and the boiling point of the reaction medium.

The intermediates A are commercially available or can be prepared by application or adaptation of the methods described in the examples, and in particular by the following methods:

When R is phenyl substituted with halogen, the intermediate A can be obtained from the corresponding halobenzaldehyde by the action of potassium hydroxide and aqueous ammonia, in the presence of lithium chloride and benzyltriethylammonium chloride, in a solvent such as a mixture of dichloromethane, chloroform and water at a temperature of between 0° C. and 30° C., optionally followed by an esterification by the action of a (1–4C) aliphatic alcohol (preferably methanol or ethanol), in the presence of an inorganic acid such as sulfuric acid, at a temperature of between 50° C. and the boiling point of the reaction medium.

When R is phenyl substituted with alkoxy, Ra is an alkyl radical and Rb is tert-butoxycarbonyl, the intermediate A can be obtained by alkylation of the corresponding N-tert-butoxycarbonylhydroxyphenylglycine by the action of an alkyl halide (for example methyl iodide), in the presence of a base such as potassium carbonate, in an inert solvent such as dimethylformamide, at a temperature of between 0° C. and 30° C.

The compounds of formula (I) for which R is a radical -alk(1C)-S-alk-Ar may also be prepared by the action of a derivative of formula:

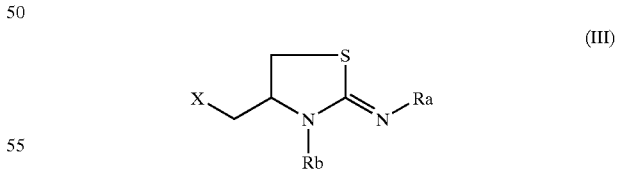

(III)

in which X is a halogen atom and preferably iodine, or a tosyl radical, Ra and Rb are hydrogen atoms or protecting groups for the amine function such as those described by T. W. Greene, Protective Groups in Organic Synthesis, J. Wiley-Interscience Publication (1991), preferably alkoxycarbonyl or acetyl and more particularly tert-butoxycarbonyl, with a derivative of formula HS-alk-Ar in which Ar represents a phenyl radical and alk is an alkylene radical (1–6C in a straight or branched chain), followed, if necessary, by a deprotection of the amine function.

This reaction is generally carried out in the presence of a base such as potassium carbonate, in a solvent such as acetonitrile or dimethylformamide and preferably acetonitrile, at a temperature of between 20° C. and the boiling point of the reaction medium.

The deprotection reaction for the compounds for which Ra or Rb is a protecting group for the amine function is carried out by any deprotection method known to those skilled in the art and in particular those described by T. W. Greene, Protective Groups in Organic Synthesis, J. Wiley-Interscience Publication (1991). Preferably, when the protecting group is an acetyl radical, this reaction is carried out using aqueous hydrochloric acid, at a temperature of 100° C. When the protecting group is a tert-butoxycarbonyl radical, this reaction is carried out using hydrochloric acid in dioxane, at a temperature in the region of 20° C.

The compounds of formula (III) may themselves be obtained according to the following reaction scheme:

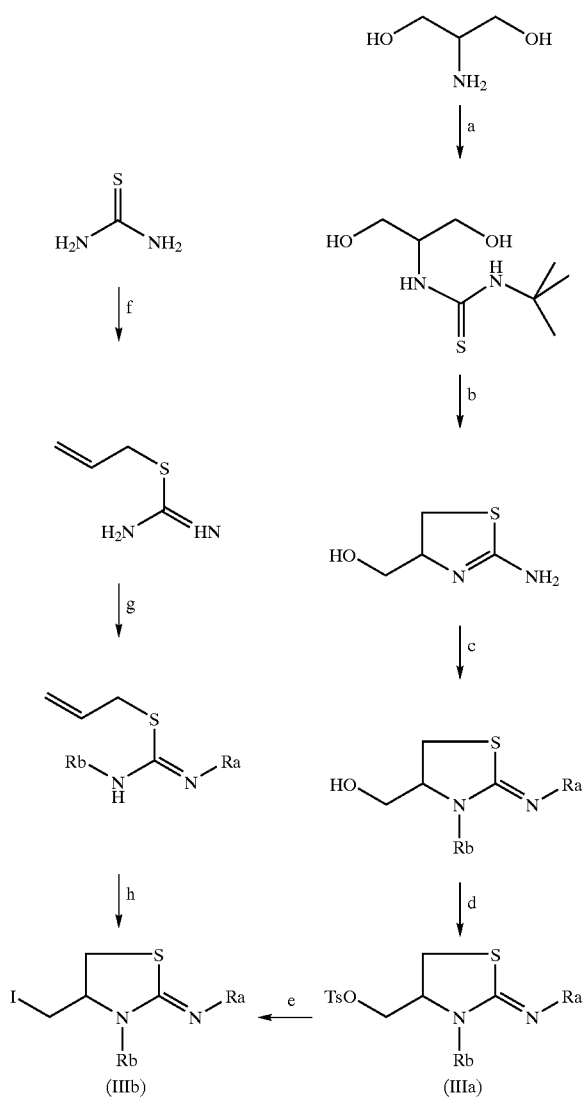

In these formulae, Ra and Rb are a hydrogen atom or a protecting group for the amine function such as those described by T. W. Greene, Protective Groups in Organic Synthesis, J. Wiley-Interscience Publication (1991), preferably alkoxycarbonyl or acetyl and more particularly tert-butoxycarbonyl, and Ts is a tosyl radical.

Reaction a is generally carried out by the action of tert-butyl isothiocyanate, in an inert solvent such as an aliphatic (1–4C) alcohol (preferably methanol or ethanol), optionally in the presence of a tertiary amine such as triethylamine, at a temperature of between 20° C. and the boiling point of the reaction medium.

Cyclization reaction b is generally carried out using an acid such as hydrochloric acid, in aqueous medium, at a temperature in the region of 100° C. 6N hydrochloric acid is preferably used.

When Ra or Rb is a tert-butoxycarbonyl group, reactions c and g are carried out by any protection method known to those skilled in the art and in particular those described by T. W. Greene, Protective Groups in Organic Synthesis, J. Wiley-Interscience Publication (1991). This reaction is preferably carried out using di-tert-butyl dicarbonate, in the presence of a base such as triethylamine and optionally in the presence of 4-(dimethylamino)pyridine, in a solvent such as dichloromethane and at a temperature in the region of 20° C., or alternatively in the presence of a base such as potassium carbonate, in a solvent such as water and at a temperature in the region of 20° C.

Reaction d is generally carried out by the action of p-toluenesulfonyl chloride, in the presence of a tertiary amine such as triethylamine, in an inert solvent such as dichloromethane, at a temperature of between 20° C. and the boiling point of the reaction medium.

Reaction e is generally carried out by the action of sodium iodide, in an inert solvent such as acetone, at a temperature of between 20° C. and the boiling point of the reaction medium.

Reaction f is generally carried out by the action of an allyl halide, for example allyl chloride, in an aliphatic (1–4C) alcohol, preferably ethanol, at a temperature of between 20° C. and the boiling point of the reaction medium.

Reaction h is generally carried out by the action of iodine, in the presence of a base such as sodium bicarbonate, in a solvent such as dichloromethane, at a temperature of between 20° C. and the boiling point of the reaction medium.

The compounds of formula (I) are isolated and can be purified by the usual known methods, for example by crystallization, chromatography or extraction.

The enantiomers of the compounds of formula (I) can be obtained by resolving the racemic mixtures, for example by chromatography on a chiral column according to Pirckle W.H. et al., Asymmetric Synthesis, Vol. 1, Academic Press (1983) or by formation of salts or by synthesis from chiral precursors. The diastereoisomers can be prepared according to the known conventional methods (crystallization or chromatography or from chiral precursors).

The compounds of formula (I) can optionally be converted into addition salts with an inorganic or organic acid by the action of such an acid in an organic solvent such as an alcohol, a ketone, an ether or a chlorinated solvent. These salts also form part of the invention.

Examples of pharmaceutically acceptable salts which may be mentioned are the following salts: benzenesulfonate, hydrobromide, hydrochloride, citrate, ethanesulfonate, fumarate, gluconate, iodate, isethionate, maleate, methanesulfonate, methylenebis-b-oxynaphthoate, nitrate, oxalate, pamoate, phosphate, salicylate, succinate, sulfate, tartrate, theophyllineacetate and p-toluenesulfonate.

The compounds of formula (I) are inhibitors of inducible NO-synthase or type-2 NO-synthase (NOS-2) and are thus useful for preventing and treating disorders associated with excessive NO production, such as multiple sclerosis, cerebral, focal or global ischemia, cerebral or spinal trauma, Parkinson's disease, Huntington's disease, Alzheimer's disease, amyotrophic lateral sclerosis, migraine, depression, schizophrenia, anxiety and epilepsy, diabetes, atherosclerosis, myocarditis, arthritis, arthrosis, asthma, irritable bowel syndrome, Crohn's disease, peritonitis, gastroesophageal reflux, uveitis, Guillain-Barre syndrome, glomerulonephritis, lupus erythematosus, psoriasis, the growth of certain forms of tumors such as, for example, epitheliomas, adenocarcinomas or sarcomas, and infections with Gram-positive or Gram-negative intracellular or extracellular bacteria.

Their activity as NOS-2 inhibitors was determined by measuring the conversion of [$^3$H]-L-arginine into [$^3$H]-L-citrulline with, respectively, an NOS-2 enzymatic fraction extracted from the lungs of rats or mice pretreated with lipopolysaccharides (10 mg/kg i.p. 6 hours before collecting the tissue). The compounds were incubated for 20 to 30 minutes at 37° C. in the presence of 5 $\mu$M of [$^3$H]-L-arginine, 1 mM of NADPH, 15 $\mu$M of tetrabiopterine, 1 $\mu$M of FAD and 0.1 mM of DTT in a HEPES buffer (50 mM, pH 6.7) containing 10 $\mu$g/ml of calmodulin. The incubation was stopped by adding cold HEPES buffer (100 mM, pH 5.5) containing 10 mM of EGTA and 500 mg of a cationic ion-exchange resin (AG50W-X8, counterion: Na$^+$) to separate the [$^3$H]-L-arginine from the [$^3$H]-L-citrulline. After separation of the phases by settling for 5 min, the radioactivity remaining in the liquid phase was measured in a scintillation counter in the presence of a suitable scintillation liquid. The yield for the recovery of the [$^3$H]-L-citrulline formed was able to be estimated using [$^{14}$C-ureido]-L-citrulline as external standard.

The activity was expressed as picomole(s) of [$^3$H]-L-citrulline formed per minute and per milligram of protein contained in the reaction medium.

In this test, the IC$_{50}$ value of the compounds of formula (I) is less than or equal to 1 $\mu$M.

The compounds of formula (I) are of low toxicity. Their LD$_{50}$ value is greater than 40 mg/kg via the subcutaneous route in mice.

The examples which follow illustrate the invention.

EXAMPLE 1

(4RS)-4-(3-Bromophenyl)-4,5-dihydro-1,3-thiazol-2-ylamine Hydrochloride

A suspension of 0.5 g of N-(tert-butyl)-N'-[2-hydroxy-1-(3-bromophenyl)ethyl]thiourea in 3.8 cm$^3$ of 6N hydrochloric acid is heated with stirring at a temperature in the region of 100° C. for 5 hours 30 minutes. The reaction medium is then cooled to a temperature in the region of 20° C. A white precipitate forms, which is filtered off after stirring for 30 minutes. The filter cake is rinsed with diethyl ether and then dried in an oven under reduced pressure (10 Pa) at a temperature in the region of 60° C., after which it is purified by chromatography, under an argon pressure of 50 kPa, on a column of silica gel (particle size 40–63$\mu$; diameter 1.5 cm; height 20 cm), eluting with a dichloromethane/methanol mixture (90/10 by volume). The fractions containing the expected product are collected. These fractions are combined and then concentrated under reduced pressure (5 kPa) at a temperature in the region of 40° C. 0.1 g of (4RS)-4-(3-bromophenyl)-4,5-dihydro-1,3-thiazol-2-ylamine hydrochloride is obtained in the form of a white solid. (R$^f$=0.26 in a 90/10 by volume dichloromethane/methanol mixture, on a Merck 60F$_{254}$R silica plate). [$^1$H NMR spectrum (250 MHz, d$_6$-(CD$_3$)SO, $\delta$ in ppm): 3.45 (dd, J=14 and 8 Hz: 1H); 3.97 (dd, J=14 and 8.5 Hz : 1H); 5.42 (dd, J=8.5 and 8 Hz: 1H); from 7.35 to 7.55 (mt: 2H); from 7.55 to 7.75 (mt: 2H); from 9.10 to 10.90 (broad unres. mult.: 1H)].

N-(tert-Butyl)-N'-[2-hydroxy-1-(3-bromophenyl)ethyl]thiourea: A solution of 3.54 g of 2-amino-2-(3-bromophenyl)-1-ethanol, in 20 cm$^3$ of ethanol containing 0.18 cm$^3$ of tert-butyl isothiocyanate is stirred at a temperature in the region of 20° C. for 5 hours. After concentration of the reaction mass under reduced pressure (5 kPa) at a temperature in the region of 40° C., the residue obtained is taken up in 25 cm$^3$ of petroleum ether. The resulting crystals are spin-filtered, washed with twice 25 cm$^3$ of petroleum ether and then dried under reduced pressure (5 kPa) at a temperature in the region of 20° C. 4 g of N-(tert-butyl)-N'-[2-hydroxy-1-(3-bromophenyl)ethyl]thiourea are obtained in the form of a white solid (R$_f$=0.68 in a 40/5/0.5 by volume dichloromethane/methanol/aqueous ammonia mixture, on a Merck 60F$_{254^R}$ silica plate)

2-Amino-2-(3-bromophenyl)-1-ethanol: A solution of 4.4 g of ethyl 3-bromophenylglycinate in 80 cm$^3$ of ethanol is maintained at a temperature in the region of 20° C. 0.97 g of sodium borohydride is added portionwise with stirring and the mixture is then stirred for 18 hours at a temperature in the region of 20° C. After concentration of the reaction medium under reduced pressure (5 kPa) at a temperature in the region of 40° C., the residue obtained is taken up in 40 cm$^3$ of water and then extracted with 3 times 50 cm$^3$ of ethyl acetate. The extracts are combined and then dried over sodium sulfate, filtered and concentrated under reduced pressure (5 kPa) at a temperature in the region of 40° C. An oil is obtained, which is purified by chromatography under an argon pressure of 50 kPa, on a column of silica gel (particle size 40–63$\mu$; diameter 2.5 cm; height of silica 35 cm), eluting with a dichloromethane/methanol mixture (90/10 by volume). The fractions containing the product are collected. These fractions are combined and then concentrated under reduced pressure (5 kPa) at a temperature in the region of 40° C. 2.1 g of 2-amino-2-(3-bromophenyl)-1-ethanol are obtained in the form of a yellow solid melting at 76° C.

Ethyl 3-bromophenylglycinate: A mixture of 21.3 g of 3-bromophenylglycine in 160 cm$^3$ of 6.5N hydrochloric ethanol is heated with stirring for 24 hours at a temperature in the region of 80° C. The reaction medium is filtered and the filter cake is then washed with twice 30 cm$^3$ of ethanol. The filtrate is concentrated under reduced pressure (5 kPa) at a temperature in the region of 40° C. An oil is obtained, which is basified by addition of aqueous sodium carbonate solution. The mixture is extracted with 3 times 100 cm$^3$ of ethyl acetate. The extracts are combined, washed with twice 100 cm$^3$ of aqueous sodium chloride solution, dried over sodium sulfate, filtered and then concentrated under reduced pressure (5 kPa) at a temperature in the region of 40° C. 4.7 g of ethyl 3-bromophenylglycinate are obtained in the form of a yellow oil. (R$_f$=0.38 in a 90/5 by volume dichloromethane/methanol mixture, on a Merck 60F$_{254}$R silica plate).

3-Bromophenylglycine: 8.4 g of lithium chloride are introduced into a stirred mixture, under an inert atmosphere, of 16.8 g of potassium hydroxide in 56 cm$^3$ of 32% aqueous ammonia, followed by addition of 2.78 g of benzyltriethylammonium chloride predissolved in 50 cm$^3$ of dichloromethane. The mixture obtained is cooled to a temperature in the region of 0° C., followed by addition thereto of 18.5 g of 3-bromobenzaldehyde predissolved in 50 cm$^3$ of dichloromethane and 12.8 cm$^3$ of chloroform, while maintaining the mixture at a temperature in the region of 0° C. The reaction medium is stirred for 6 hours at this temperature and then for 18 hours at a temperature in the region of 20° C. The insoluble material is filtered off and the filtrate is then separated out after settling has taken place. The aqueous phase is separated out, washed with twice 50 cm³ of dichloromethane and acidified with 10 cm³ of concentrated hydrochloric acid to obtain a pH of 7. The acidification is completed up to pH 6 by a further addition of aqueous 1N hydrochloric acid. The expected acid precipitates after scratching. The mixture is stirred for 1 hour at a temperature in the region of 5° C., and is then filtered. The crystals obtained are washed with 5 cm³ of water and dried in an oven under reduced pressure (10 Pa) at a temperature in the region of 60° C. 0.41 g of 3-bromophenylglycine is obtained in the form of a white solid. [Infrared spectrum (KBr): 3080; 2980; 2670; 1635; 1580; 1400; 1355; 775 and 695 cm$^{-1}$].

EXAMPLE 2

4-(4-Methoxyphenyl)-4,5-dihydro-1,3-thiazol-2-ylamine oxalate

A mixture of 1.3 g of N-(tert-butyl)-N'-[1-(4-methoxyphenyl)-2-hydroxyethyl]thiourea in 12.3 cm³ of aqueous 6N hydrochloric acid is heated with stirring at a temperature in the region of 100° C. for 1 hour. The dense oil which precipitates is separated out after settling from the supernatant hydrochloric aqueous phase. After cooling to about 20° C., this aqueous phase is extracted with 5 cm³ of ethyl acetate and the resulting aqueous phase is then evaporated under reduced pressure (5 kPa) at a temperature in the region of 50° C. An oil is obtained, which is freed of its residual water by azeotropic entrainment first with 10 cm³ of ethanol and then with 10 cm³ of diethyl ether, each repetition being followed by concentrating under the above conditions. 6 cm³ of 1N sodium hydroxide are added to the oil obtained and the mixture is then extracted with 30 cm³ of diethyl ether containing 15 cm³ of ethyl acetate. The organic phase is separated out after settling has taken place and evaporated under reduced pressure (5 kPa) at a temperature in the region of 40° C. 0.1 g of oxalic acid predissolved in 1 cm³ of acetone is added to the residue obtained. The white precipitate formed is separated out by filtration, washed once with acetone, twice with chloroform and then once with ethyl acetate, and dried under reduced pressure (10 Pa) at a temperature in the region of 40° C. 0.063 g of 4-(4-methoxyphenyl)-4,5-dihydro-1,3-thiazol-2-ylamine is obtained in the form of a white solid melting at 180° C. [$^1$H NMR spectrum (300 MHz, d$_6$-(CD$_3$)SO, δ in ppm): 3.40 (dd, J=14 and 8.5 Hz 1H); 3.80 (s: 3H); 3.93 (dd, J=14 and 8.5 Hz: 1H); 4.22 (unres. mult.: 2H); 3.58 (t, J=8.5 Hz : 1H); 7.00 (d, J=8.5 Hz: 2H); 7.34 (d, J=8.5 Hz : 2H)].

N-(tert-Butyl)-N'-[1-(4-methoxyphenyl)-2-hydroxyethyl] thiourea: The process is performed under the conditions of Example 1, starting with 1.3 g of 2-amino-2-(4-methoxyphenyl)-1-ethanol and 1.46 cm³ of tert-butyl isothiocyanate in 12 cm³ of absolute ethanol for 21 hours at a temperature in the region of 20° C. After concentration of the reaction mass under reduced pressure (5 kPa) at a temperature in the region of 40° C., the residue obtained is taken up in 10 cm³ of water. A crystalline precipitate forms, which is filtered off, washed with 3 times 5 cm³ of diethyl ether and dried under reduced pressure (10 Pa) at a temperature in the region of 40° C. 1.32 g of N-(tert-butyl)-N'-[1-(4-methoxyphenyl)-2-hydroxyethyl]thiourea are obtained in the form of a white solid melting at 127° C.

2-Amino-2-(4-methoxyphenyl)-1-ethanol: A mixture of 3.4 g of tert-butyl 1-(4-methoxyphenyl)-2-hydroxyethylcarbamate in 32 cm³ of methanol containing 10% by mass of anhydrous hydrogen chloride is stirred for 1 hour at a temperature in the region of 20° C. The reaction medium is concentrated under reduced pressure (5 kPa) at a temperature in the region of 40° C. The residue is taken up in 9 cm³ of aqueous 5% sodium hydrogen carbonate solution and the mixture is then extracted with 3 times 30 cm³ of dichloromethane. The aqueous phase is concentrated as above and the white solid obtained is then taken up in 17 cm³ of aqueous 1N sodium hydroxide solution. The precipitate is extracted with 3 times 30 cm³ of dichloromethane. The combined organic extracts are evaporated under reduced pressure (5 kPa) at a temperature in the region of 40° C. The white solid obtained is dried under reduced pressure (10 Pa) at a temperature in the region of 40° C. 1.3 g of 2-amino-2-(4-methoxyphenyl)-1-ethanol are obtained in the form of a white solid melting at 96° C. tert-Butyl 1-(4-methoxyphenyl)-2-hydroxyethylcarbamate: 2.24 g of lithium chloride are added to a solution of 7.8 g of methyl N-Boc-(4-methoxyphenyl)glycinate in 35 cm³ of tetrahydrofuran cooled to a temperature of 0° C., followed by portionwise addition of 1.99 g of sodium borohydride and finally 74 cm³ of ethanol. The temperature is allowed to return to about 20° C. and the reaction is then completed by stirring the mixture for 18 hours at this same temperature. The medium is re-cooled to about 5° C. and a sufficient amount of aqueous 1M sodium hydrogen sulfate solution to give a pH in the region of 2 is then added thereto. The mixture is stirred for 3 hours and is then evaporated under reduced pressure (5 kPa) at a temperature in the region of 50° C. 60 cm³ of dichloromethane and 30 cm³ of aqueous 1M sodium hydrogen sulfate solution are added to the residue obtained. After stirring the mixture and then separating out the organic phase after settling of the phases has taken place, the aqueous phase is extracted with twice 30 cm³ of dichloromethane. The combined organic extracts are dried over sodium sulfate and concentrated as above. A white solid is obtained, which is taken up in 30 cm³ of cyclohexane and filtered. The crystals are dried under reduced pressure (10 Pa) at a temperature in the region of 60° C. 3.47 g of tert-butyl 1-(4-methoxyphenyl)-2-hydroxyethylcarbamate are obtained in the form of a white solid melting at 130° C.

Methyl N-Boc-(4-methoxyphenyl)glycinate: 10.45 g of potassium carbonate are added to a stirred solution, cooled to a temperature in the region of 0° C., of 8.25 g of N-Boc-(4-hydroxyphenyl)glycine in 112 cm³ of anhydrous dimethylformamide, followed by dropwise addition of 4.7 cm³ of methyl iodide. The mixture is stirred at a temperature in the region of 20° C. for 18 h 30 min. After addition of 280 cm³ of diethyl ether and 140 cm³ of water, the ether phase is separated out after settling has taken place and is then washed successively with 140 cm³ of water, 140 cm³ of aqueous 1M sodium hydrogen sulfate solution and 140 cm³ of saturated sodium chloride solution. The organic phase is dried over sodium sulfate and evaporated under reduced pressure (5 kPa) at a temperature in the region of 40° C. 7.88 g of methyl N-Boc-(4-methoxyphenyl)-glycinate are obtained in the form of an oil which crystallizes rapidly. ($R_f$=0.28 in a 30/20 by volume cyclohexane/diethyl ether mixture, on a Merck 60F$_{254}$$^R$ silica plate).

N-Boc-(4-Hydroxyphenyl)glycine: 12 g of di-tert-butyl dicarbonate are added, at a temperature in the region of 20° C., to a stirred solution of 7.55 g of 4-hydroxyphenylglycine in 53.2 cm³ of aqueous 1N sodium hydroxide solution and the mixture is then stirred for 4 hours at a temperature in the region of 15° C. After leaving the reaction medium to stand for 16 hours at a temperature in the region of 20° C., it is washed with twice 30 cm³ of diethyl ether. The aqueous phase is separated out after settling of the phases has taken place, and 73 cm³ of aqueous 1M sodium hydrogen sulfate solution are then added thereto with stirring. The mixture is extracted with twice 135 cm³ of dichloromethane. The organic extracts are combined, dried over sodium sulfate and concentrated under reduced pressure (5 kPa) at a temperature in the region of 40° C. A white foam is obtained, which is taken up in 60 cm³ of water and spin-filtered. The solid obtained is dried under reduced pressure (10 Pa) at a temperature in the region of 20° C. 9.26 g of N-Boc-(4-hydroxyphenyl)glycine are obtained in the form of a white solid melting at 110° C.

EXAMPLE 3

(−)-(4R)-4-(4-Methoxyphenyl)-4,5-dihydro-1,3-thiazol-2-ylamine Hydrochloride The process is performed under the conditions of Example 1, starting with 2.5 g of N-(tert-butyl)-N'-[(1R)-1-(4-methoxyphenyl)-2-hydroxyethyl]thiourea in 25 cm³ of aqueous 6N hydrochloric acid for 3 hours at a temperature in the region of 100° C. The reaction mass is evaporated under reduced pressure (5 kPa) at a temperature in the region of 50° C. 15 cm³ of aqueous 1N sodium hydroxide and 5 cm³ of water are added to the residue obtained. The mixture is extracted with 20 cm³ of ethyl acetate and the organic phase is then concentrated as above. The product obtained is purified by chromatography, under an argon pressure of 50 kPa, on a column of silica gel (particle size 40–63μ; mass of silica 80 g), eluting with an ethyl acetate/methanol mixture (80/20 by volume), and collecting about 10 cm³ fractions. Fractions 10 to 16 are combined and then evaporated under reduced pressure (5 kPa) at a temperature in the region of 40° C. 0.23 g of a lacquer is obtained, the hydrochloride of which is prepared in the following way: the product is dissolved in 2.5 cm³ of acetone and 1 cm³ of diethyl ether, followed by addition thereto of 2 cm³ of 4.5N hydrochloric ether. A crystalline product precipitates. It is filtered off, washed 3 times with acetone and then dried at a temperature in the region of 40° C. under reduced pressure (10 Pa). 0.09 g of (−)-(4R)-4-(4-methoxyphenyl)-4,5-dihydro-1,3-thiazol-2-ylamine hydrochloride is obtained in the form of a white solid melting at 236° C. ($\alpha_D^{20}$=−79.6±1.3 at a concentration of 0.5% in methanol).

N-(tert-Butyl)-N'-[(1R)-1-(4-methoxyphenyl)2-hydroxyethyl]thiourea: The process is performed under the conditions of Example 1, starting with 5.78 g of (2R)-2-amino-2-(4-methoxyphenyl)-1-ethanol and 6.48 cm³ of tert-butyl isothiocyanate in 73 cm³ of ethanol for 17 h 30 minutes at a temperature in the region of 20° C. The reaction mass is evaporated under reduced pressure (5 kPa) at a temperature in the region of 40° C. and the solid residue obtained is then ground in 45 cm³ of water, filtered and washed with twice 20 cm³ of water and twice 25 cm³ of diethyl ether. The crystals are dried in an oven under reduced pressure (10 Pa) at a temperature in the region of 45° C. 4.9 g of N-(tert-butyl)-N'-[(1R)-1-(4-methoxyphenyl)2-hydroxyethyl]-thiourea are obtained in the form of a white solid. ($R_f$=0.60 in ethyl acetate, on a Merck 60F$_{254}$R silica plate).

(2R)-2-Amino-2-(4-methoxyphenyl)-1-ethanol: The process is performed under the conditions of Example 2, starting with 12.45 g of tert-butyl (1R)-1-(4-methoxyphenyl)-2-hydroxyethylcarbamate in 130 cm³ of 2.5N hydrochloric methanol, with stirring for 1 h 30 minutes at a temperature in the region of 20° C., and then for 30 minutes at a temperature in the region of 30° C. The reaction mass is evaporated under reduced pressure (5 kPa) at a temperature in the region of 40° C. 61 cm³ of aqueous 5% sodium hydrogen carbonate solution are added to the residue obtained and the mixture is then extracted with 3 times 100 cm³ of dichloromethane. The aqueous phase is separated out after settling has taken place and is then evaporated as above. The solid obtained is taken up in 65 cm³ of aqueous 1N sodium hydroxide solution and the resulting solution is reduced to ⅔ of its volume by concentration under the above conditions. The mixture is extracted with 3 times 100 cm³ of dichloromethane. The extracts are combined, dried over magnesium sulfate, filtered and evaporated under reduced pressure (5 kPa) at a temperature in the region of 40° C. The crystals obtained are dried under reduced pressure (5 kPa) at about 20° C. 5.86 g of (2R)-2-amino-2-(4-methoxyphenyl)-1-ethanol are obtained in the form of a white solid melting at 103° C. tert-Butyl (1R)-1-(4-methoxyphenyl)-2-hydroxyethylcarbamate: The process is performed under the conditions of Example 2, starting with 15.6 g of methyl N-Boc-D-(4-methoxyphenyl)glycinate dissolved in 70 cm³ of anhydrous tetrahydrofuran, and in the presence of 4.48 g of lithium chloride. The portionwise addition of 3.98 g of sodium borohydride is carried out at a temperature in the region of 0° C. After addition of 148 cm³ of absolute ethanol at this same temperature, the temperature is allowed to return to about 20° C. and stirring is continued for 20 hours. After cooling the reaction mass to a temperature in the region of 5° C., 98 cm³ of aqueous 1M sodium hydrogen sulfate solution are added. The mixture is stirred for 3 hours and is then evaporated under reduced pressure (5 kPa) at a temperature in the region of 40° C. The residue is taken up in 220 cm³ of dichloromethane, 70 cm³ of aqueous 1M sodium hydrogen sulfate solution and 30 cm³ of water. The mixture is stirred and then the phases are allowed to separate by settling. The organic phase is separated out and the aqueous phase is extracted with twice 60 cm³ of dichloromethane. The organic extracts are combined and then dried over sodium sulfate, filtered and then evaporated under reduced pressure (5 kPa) at a temperature in the region of 40° C. A solid is obtained, which is taken up in 50 cm³ of cyclohexane; the crystals are then spin-filtered and dried in an over under reduced pressure (10 Pa) at a temperature in the region of 60° C. 12.47 g of tert-butyl (1R)-1-(4-methoxyphenyl)-2-hydroxyethylcarbamate are obtained in the form of a white solid melting at 138° C.

Methyl N-Boc-D-(4-methoxyphenyl)glycinate: The process is performed as in Example 2, starting with a solution of 30.8 g of N-Boc-D-(4-hydroxyphenyl)-glycine in 418 cm³ of anhydrous dimethylformamide, cooled to a temperature in the region of 0° C., to which is added 17.5 cm³ of methyl iodide in the presence of 39 g of potassium carbonate. The reaction medium is returned to a temperature in the region of 20° C. and is then stirred for 22 hours at this same temperature. 1 liter of diethyl ether and 500 cm³ of water are added to the mixture. The ether phase is separated out after settling of the phases has taken place and is washed with 500 cm³ of water and then evaporated under reduced pressure (5 kPa) at a temperature in the region of 40° C. 31.53 g of methyl N-Boc-D-(4-methoxyphenyl)-glycinate are obtained in the form of a yellow oil which crystallizes rapidly. ($R_f$=0.30 in 30/20 cyclohexane/diethyl ether, on a Merck 60F$_{254}$R silica plate).

N-Boc-D-(4-Hydroxyphenyl)glycine: The process is performed under the conditions of Example 2, starting with a solution of 30.2 g of D-(−)-(4-hydroxyphenyl)glycine in 213 cm³ of aqueous 1N sodium hydroxide solution and 48 g of di-tert-butyl dicarbonate, stirred for 4 hours at a temperature in the region of 20° C. The reaction medium is washed with twice 120 cm³ of diethyl ether and the aqueous phase is then separated out after settling has taken place and 392 cm³ of aqueous 1M sodium hydrogen sulfate solution are added, the amount required to obtain a pH in the region of 1. 450 cm³ of dichloromethane are added and, after shaking the mixture, the organic phase is separated out after settling of the phases has taken place. The aqueous phase is extracted twice more with 450 cm³ of dichloromethane. The organic extracts are combined, dried over sodium sulfate and then concentrated under reduced pressure (5 kPa) at a temperature in the region of 40° C. A residue is obtained, which is taken up in 240 cm³ of water. The resulting crystals are spin-filtered and then dried under reduced pressure (10 Pa) at a temperature in the region of 40° C. 9.59 g of N-Boc-D-(4-hydroxyphenyl)-glycine are obtained in the form of a white solid. [¹H NMR spectrum (300 MHz, $d_6$-$(CD_3)SO$, δ in ppm): 1.38 (s 9H); 4.98 (d, J=9 Hz: 1H); 6.73 (d, J=8 Hz: 2H); 7.20 (d, J=8 Hz: 2H); 7.41 (d, J=9 Hz, 1H); 9.48 (unres. mult.: 1H)].

EXAMPLE 4

(−)-(4R)-4-Phenyl-4,5-dihydro-1,3-thiazol-2-ylamine Hydrochloride

The process is performed under the conditions of Example 1, starting with 2.4 g of N-(tert-butyl)-N'-[(1R)-2-hydroxy-1-phenylethyl]thiourea in 24 cm³ of aqueous 6N hydrochloric acid for 1 hour 30 minutes at a temperature in the region of 100° C. After cooling the medium to a temperature in the region of 0° C., the precipitate formed is filtered off and the filter cake is then washed with 7 cm³ of aqueous 6N hydrochloric acid and twice 15 cm³ of diethyl ether. The solid obtained is dried in an oven under reduced pressure (10 Pa) at a temperature in the region of 60° C. 1.6 g of (−)-(4R)-4-phenyl-4,5-dihydro-1,3-thiazol-2-ylamine hydrochloride are obtained in the form of a white solid melting at 260° C. ($\alpha_d^{20}$=−109.6±1.3 at a concentration of 1% in methanol).

N-(tert-Butyl)-N'-[(1R)-2-hydroxy-1-phenylethyl]thiourea: The process is performed under the conditions of Example 1, starting with 2.74 g of (R)-(−)-2-amino-2-phenylethanol and 2.8 cm³ of tert-butyl isothiocyanate in 15 cm³ of ethanol for 20 hours at a temperature in the region of 20° C. The reaction medium is concentrated under reduced pressure (5 kPa) at a temperature in the region of 50° C. A yellow oil is obtained, which is dissolved in 100 cm³ of ethyl acetate and the organic solution is then washed with twice 50 cm³ of aqueous sodium hydrogen carbonate solution and twice with aqueous sodium chloride solution. After drying over sodium sulfate, the organic solution is filtered and then concentrated under reduced pressure (5 kPa) at a temperature in the region of 40° C. 4.9 g of N-(tert-butyl)-N'-[(1R)-2-hydroxy-1-phenylethyl]thiourea are obtained in the form of a yellow solid melting at 98° C.

EXAMPLE 5

(4RS)-4-Benzylsulfanylmethyl-4,5-dihydrothiazol-2-ylamine Hydrochloride

A suspension of 0.1 g of N-tert-butyl-N'-[(4RS)-4-benzylsulfanylmethyl-4,5-dihydrothiazol-2-yl]amine in 5 cm³ of 5N hydrochloric acid is heated at a temperature in the region of 100° C. for 2 hours. After cooling to room temperature, the reaction mixture is concentrated under reduced pressure (1 kPa) at a temperature in the region of 50° C. The oil obtained is slurried in 5 cm³ of diethyl ether and the solid obtained is then filtered off and dried in a desiccator under reduced pressure (0.1 kPa) at a temperature in the region of 40° C. 0.06 g of (4RS)-4-benzylsulfanyl-methyl-4,5-dihydrothiazol-2-ylamine hydrochloride is obtained in the form of a cream-colored solid [¹H NMR spectrum (300 MHz, $d_6$-$(CD_3)_2SO$, δ in ppm): 2.74 (d, J=6 Hz: 2H); 3.37 (dd, J=11.5 and 5.5 Hz : 1H); 3.71 (dd, J=11.5 and 8 Hz: 1H); 3.85 (s: 2H); 4.45 (mt 1H); from 7.25 to 7.45 (mt: 5H); from 9.00 to 9.90 (very broad unresolved complex: 2H); 10.03 (unresolved complex: 1H)].

N-tert-Butyl-N'-[(4RS)-4-benzylsulfanylmethyl-4,5-dihydrothiazol-2-yl]amine: 0.28 g of potassium carbonate and 0.13 cm³ of benzyl mercaptan are added with stirring, at a temperature in the region of 20° C., to a solution of 0.39 g of tert-butyl N-[(4RS)-4-p-toluenesulfonylmethyl-4,5-dihydrothiazol-2-yl]-carbamate. After stirring for 40 hours at a temperature in the region of 20° C., the reaction mixture is filtered. The filtrate is concentrated under reduced pressure (1 kPa) at a temperature in the region of 50° C. The residue obtained is purified by chromatography under atmospheric pressure on a column of silica gel (particle size 40–60 g), eluting with a mixture of cyclohexane/ethyl acetate (75/25 by volume) and collecting 20 cm³ fractions. The fractions containing the expected product are combined and then concentrated under the above conditions. 11 g of N-tert-butyl-N'-[(4RS)-4-benzylsulfanylmethyl-4,5-dihydrothiazol-2-yl]amine are obtained in the form of a cream-colored lacquer [¹H NMR spectrum (300 MHz, d6-$(CD_3)_2SO$, δ in ppm): 1.41 (s: 9H); from 2.50 to 2.70 (mt: 2H); 3.01 (dd, J=11 and 6 Hz: 1H); from 3.25 to 3.40 (mt 1H); 3.82 (s: 2H); 4.13 (mt : 1H); from 7.20 to 7.40 (mt: 5H); from 9.40 to 9.80 (very broad unresolved complex: 1H)].

tert-Butyl N-[(4RS)-4-p-toluenesulfonylmethyl-4,5-dihydrothiazol-2-yl]carbamate: a solution of 0.8 g of tert-butyl N-[(4RS)-4-hydroxymethyl-4,5-dihydrothiazol-2-yl] carbamate, 0.76 g of p-toluene-sulfonyl chloride and 0.56 cm³ of triethylamine in 25 cm³ of dichloromethane is stirred for 16 hours at a temperature in the region of 20° C. The solution obtained is concentrated under reduced pressure (1 kPa) at a temperature in the region of 40° C. The evaporation residue obtained is purified by chromatography under atmospheric pressure on a column of silica gel (particle size 60–200μ; diameter 2 cm; height 25 cm), eluting with a mixture of cyclohexane/ethyl acetate (70/30 by volume) and collecting 30 cm³ fractions. The fractions containing the expected product are combined and then concentrated under the above conditions. 0.8 g of tert-butyl N-[(4RS)-4-p-toluenesulfonylmethyl-4,5-dihydrothiazol-2-yl]carbamate is obtained in the form of a white solid [¹H NMR spectrum (300 MHz, $CDCl_3$, δ in ppm): 1.48 (s: 9H); 2.46 (s: 3H); 3.10 (dd, J=11.5 and 5.5 Hz: 1H); 3.33 (dd, J=11.5 and 8.5 Hz: 1H); 3.97 (dd, J=9.5 and 8 Hz: 1H); 4.06 (dd, J=9.5 and 4.5 Hz: 1H); 4.43 (mt: 1H); 7.36 (d, J=8 Hz: 2H); 7.80 (d, J=8 Hz: 2H); from 8.50 to 9.40 (very broad unresolved complex: 1H)].

tert-Butyl N-[(4RS)-4-hydroxymethyl-4,5-dihydrothiazol-2-yl]carbamate: 10 cm³ of aqueous 1N sodium hydroxide are added to a solution of 2 g of tert-butyl 2-[(tert-butoxycarbonyl)imino]-(4RS)-4-[(tert-butoxycarbonyl)-oxy]methyl-1,3-thiazolidine-3-carboxylate in 20 cm³ of methanol, and the mixture is then stirred at a temperature in the region of 20° C. for 4 hours. The reaction mixture is concentrated under reduced pressure (1 kPa) at a temperature in the region of 50° C. The residue obtained is taken up in 30 cm³ of water, filtered and washed with ethyl acetate and then with water. 0.37 g of tert-butyl N-[4-(R,S)

(hydroxymethyl)-4,5-dihydrothiazol-2-yl]carbamate is obtained in the form of a white solid [mass spectrum: DCI m/z=233, MH+ m/z=177 (M-$C_4H_7$)+].

tert-Butyl 2-[(tert-butoxycarbonyl)imino]-(4RS)-4-[(tert-butoxycarbonyl)oxy]methyl-1,3-thiazolidine-3-carboxylate: 10.91 g of di-tert-butyl dicarbonate and 2.81 cm³ of triethylamine are added to a solution of 1.98 g of (4RS)-4-hydroxymethyl-4,5-dihydrothiazol-2-ylamine in 20 cm³ of dichloromethane and the mixture is then stirred at a temperature in the region of 20° C. After 4 hours, a further 3 cm³ of triethylamine are added and the mixture is then stirred for 16 hours at a temperature in the region of 20° C. 50 cm³ of water are added to the reaction mixture, the phases are separated out after settling has taken place and the organic phase is dried over magnesium sulfate, filtered and concentrated under reduced pressure (1 kPa) at a temperature in the region of 40° C. 7 g of tert-butyl 2-[(tert-butoxycarbonyl)imino]-(4RS)-4-1(tert-butoxycarbonyl)oxy]methyl-1,3-thiazolidine-3-carboxylate are obtained in the form of an oil [mass spectrum: DCI m/z=433, MH+ m/z=333 (M-$C_5H_7O_2$)+].

(4RS)-4-Hydroxymethyl-4,5-dihydrothiazol-2-ylamine: a solution of 90 g of 1-tert-butyl-3-(2-hydroxy-1-hydroxymethylethyl)thiourea in 500 cm³ of 6N hydrochloric acid is stirred at a temperature in the region of 100° C. After 3 hours, the reaction mixture is cooled to about 20° C. and is then concentrated under reduced pressure (1 kPa) at a temperature in the region of 50° C. The residue obtained is taken up in 100 cm³ of water, basified with 100 cm³ of 5N sodium hydroxide and then concentrated as above. The oil obtained is stirred for 20 hours at a temperature in the region of 20° C. in 300 cm³ of ethanol, filtered and washed with 5 times 50 cm³ of ethanol and then with 3 times 100 cm³ of methanol. The various filtrates are combined, evaporated under reduced pressure (1 kPa) at a temperature in the region of 40° C. and then crystallized from 400 cm³ of ethanol to give 31 g of (4RS)-4-hydroxy-methyl-4,5-dihydrothiazol-2-ylamine in the form of a white solid melting at 122° C. [Infrared spectrum (KBr): 3311; 3164; 1648; 1601; 1349; 1051 and 982 cm$^{-1}$].

1-tert-Butyl-3-(2-hydroxy-1-hydroxymethyl-ethyl)thiourea: 30.4 cm³ of butyl isothiocyanate are added to a solution of 14.6 g of 2-amino-1,3-propanediol in 245 cm³ of ethanol, and the mixture is then stirred at a temperature in the region of 20° C. for 94 hours. The reaction medium is concentrated under reduced pressure (5 kPa) at a temperature in the region of 40° C., slurried in a mixture of 160 cm³ of petroleum ether and 26 cm³ of ethanol, filtered and then dried in a desiccator under reduced pressure (0.1 kPa) at a temperature in the region of 60° C. 30 g of 1-tert-butyl-3-(2-hydroxy-1-hydroxymethylethyl)thiourea are obtained in the form of a white solid [¹H NMR spectrum (250 MHz, $d_6$-$(CD_3)_2SO$, δ in ppm): 1.42 (s : 9H); 3.38 (mt: 2H); 3.54 (mt: 2H); 4.17 (unresolved complex: 1H); 4.70 (t, J=5 Hz: 2H); 7.08 (d, J=8 Hz: 1H); 7.38 (s: 1H)].

The medicinal products according to the invention consist of a compound of formula (I) or an isomer or tautomer or salt of such a compound, in pure form or in the form of a composition in which it is combined with any other pharmaceutically compatible product, which may be inert or physiologically active. The medicinal products according to the invention may be used orally, parenterally, rectally or topically.

Solid compositions for oral administration which can be used include tablets, pills, powders (gelatin capsules, cachets) or granules. In these compositions, the active principle according to the invention is mixed with one or more inert diluents, such as starch, cellulose, sucrose, lactose or silica, under a stream of argon. These compositions can also comprise substances other than diluents, for example one or more lubricants such as magnesium stearate or talc, a dye, a coating (dragees) or a varnish.

Liquid compositions for oral administration that can be used include pharmaceutically acceptable solutions, suspensions, emulsions, syrups and elixirs containing inert diluents such as water, ethanol, glycerol, plant oils or liquid paraffin. These compositions can comprise substances other than diluents, for example wetting products, sweeteners, thickeners, flavorings or stabilizers.

The sterile compositions for parenteral administration can preferably be aqueous or non-aqueous solutions, suspensions or emulsions. Solvents or vehicles which may be used include water, propylene glycol, a polyethylene glycol, plant oils, in particular olive oil, injectable organic esters, for example ethyl oleate, or other suitable organic solvents. These compositions can also contain adjuvants, in particular wetting agents, isotonic agents, emulsifiers, dispersants and stabilizers. The sterilization can be carried out in several ways, for example by aseptic filtration, by incorporating sterilizing agents into the composition, by irradiation or by heating. They can also be prepared in the form of sterile solid compositions which can be dissolved at the time of use in sterile water or any other injectable sterile medium.

The compositions for rectal administration are suppositories or rectal capsules which contain, besides the active product, excipients such as cocoa butter, semisynthetic glycerides or polyethylene glycols.

Compositions for topical administration can be, for example, creams, lotions, eye drops, mouth washes, nasal drops or aerosols.

In human therapy, the compounds according to the invention are particularly useful for treating and/or preventing multiple sclerosis, cerebral, focal or global ischemia, cerebral or spinal trauma, Parkinson's disease, Huntington's disease, Alzheimer's disease, amyotrophic lateral sclerosis, migraine, depression, schizophrenia, anxiety, epilepsy, diabetes, atherosclerosis, myocarditis, arthritis, arthrosis, asthma, irritable bowel syndrome, Crohn's disease, peritonitis, gastro-esophageal reflux, uveitis, Guillain-Barre syndrome, glomerulonephritis, lupus erythematosus, psoriasis, the growth of certain forms of tumors such as, for example, epitheliomas, adenocarcinomas or sarcomas, and in infections with Gram-positive or Gram-negative intracellular or extracellular bacteria.

The doses depend on the desired effect, the duration of the treatment and the route of administration used; they are generally between 1 mg and 100 mg per day via the oral route for an adult, with unit doses ranging from 0.5 mg to 50 mg of active substance.

In general, the doctor will determine the appropriate dosage as a function of the age, weight and all the other personal factors of the individual to be treated.

The examples which follow illustrate compositions according to the invention:

EXAMPLE A

Gel capsules containing a 50 mg dose of active product and having the composition below are prepared, according to the usual technique:

| | |
|---|---|
| - Compound of formula (I) | 50 mg |
| - Cellulose | 18 mg |
| - Lactose | 55 mg |
| - Colloidal silica | 1 mg |
| - Sodium carboxymethylstarch | 10 mg |
| - Talc | 10 mg |
| - Magnesium stearate | 1 mg |

EXAMPLE B

Tablets containing a 50 mg dose of active product and having the composition below are prepared according to the usual technique:

| | |
|---|---|
| - Compound of formula (I) | 50 mg |
| - Lactose | 104 mg |
| - Cellulose | 40 mg |
| - Polyvidone | 10 mg |
| - Sodium Carboxymethylstarch | 22 mg |
| - Talc | 10 mg |
| - Magnesium stearate | 2 mg |
| - Colloidal silica | 2 mg |
| - Mixture of hydroxymethylcellulose, glycerol and titanium oxide (72/3.5/24.5) qs 1 finished film-coated tablet weighing 245 mg | |

EXAMPLE C

An injectable solution containing 10 mg of active product and having the composition below is prepared:

| | |
|---|---|
| - Compound of formula (I) | 10 mg |
| - Benzoic acid | 80 mg |
| - Benzyl alcohol | 0.06 ml |
| - Sodium benzoate | 80 mg |
| - 95% ethanol | 0.4 ml |
| - Sodium hydroxide | 24 mg |
| - Propylene glycol | 1.6 ml |
| - Water qs | 4 ml |

The present invention also relates to the use of a compound of formula (I), the racemic mixture, enantiomers, diastereoisomers and mixtures thereof, the tautomeric form thereof and pharmaceutically acceptable salts thereof for the preparation of pharmaceutical compositions for preventing and treating diseases in which an abnormal production of nitric oxide (NO) by induction of inducible NO-synthase (NOS-2) is involved.

The present invention also relates to the method for preventing and treating diseases in which an abnormal production of nitric oxide (NO) by induction of inducible NO-synthase (NOS-2 or iNOS) is involved, by administering a compound of formula (I), the racemic mixture, enantiomers, diastereoisomers and mixtures thereof, the tautomer thereof and pharmaceutically acceptable salts thereof.

What is claimed is:

1. A pharmaceutical composition comprising, as an active ingredient, a compound of formula (I):

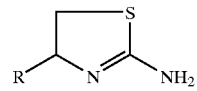

(I)

wherein R represents an -alk-S-alk-Ar radical, a phenyl radical or a phenyl radical substituted with one or more substituents of $C_{1-6}$alkoxy or halogen, and wherein Ar represents a phenyl radical and alk represents an $C_{1-6}$alkylene radical, or a racemic mixture, an enantiomer or a diastereoisomer thereof or mixtures thereof, or tautomer thereof or a pharmaceutically acceptable salt thereof and in combination with a pharmaceutically acceptable carrier.

2. The pharmaceutical composition according to claim 1, wherein R is a phenyl radical or a phenyl radical monosubstituted with $C_{1-6}$alkoxy or halogen or a racemic mixture, an enantiomer or a diastereoisomer thereof or mixtures thereof, or tautomer thereof or a pharmaceutically acceptable salt thereof.

3. The pharmaceutical composition according to claim 2, wherein R is a phenyl monosubstituted with $C_{1-6}$alkoxy or halogen at position 3 or 4.

4. The pharmaceutical composition according to claim 1 wherein the halogen is bromine.

5. The pharmaceutical composition according to claim 2 wherein the halogen is bromine.

6. The pharmaceutical composition according to claim 3 wherein the halogen is bromine.

7. The pharmaceutical composition according to claim 1 wherein the $C_{1-6}$alkoxy is methoxy.

8. The pharmaceutical composition according to claim 2 wherein the $C_{1-6}$alkoxy is methoxy.

9. The pharmaceutical composition according to claim 3 wherein the $C_{1-6}$alkoxy is methoxy.

10. The pharmaceutical composition according to claim 1 wherein the compound of formula (I) is selected from the group consisting of:

4-(3-bromophenyl)-4,5-dihydro-1,3-thiazol-2-ylamine, 4-(4-methoxyphenyl)-4,5-dihydro-1,3-thiazol-2-ylamine, 4-phenyl-4,5-dihydro-1,3-thiazol-2-ylamine and 4-(benzylsulfanylmethyl)-4,5-dihydro-1,3-thiazol-2-ylamine, or a racemic mixture, enantiomer or diastereoisomer thereof or mixtures thereof, or tautomer thereof or a pharmaceutically acceptable salt thereof.

11. The pharmaceutical composition according to claim 1 wherein the compound of formula (I) is selected from the group consisting of:

(4RS)-4-(3-bromophenyt)-4,5-dihydro-1,3-thiazol-2-ylamine, 4-(4-methoxyphenyl)-4,5-dihydro-1,3-thiazol-2-ylamine, (−)-(4R)4-(4methoxyphenyl)4,5-dihydro-1,3-thiazol-2-yl amine and (−)-(4R)4-phenyl-4,5-dihydro-1,3-thiazol-2ylamine, or a tautomer thereof or a pharmaceutically acceptable salt thereof.

12. A compound of formula (I):

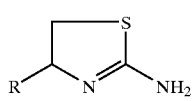

(I)

wherein R represents an -alk-S-alk-Ar radical, or a phenyl radical substituted with one or more substituents of $C_{1-6}$alkoxy or halogen, and wherein Ar represents a phenyl radical and alk represents an $C_{1-6}$alkylene radical, or a racemic mixture, an enantiomer or a diastereoisomer thereof or mixtures thereof, or tautomer thereof or a pharmaceutically acceptable salt thereof.

13. The compound according to claim 12, which is chosen from the following:

4-(3-bromophenyl)-4,5-dihydro-1,3-thiazol-2-ylamine, 4-(4-methoxyphenyl)-4,5-dihydro-1,3-thiazol-2-ylamine, 4-(benzylsulfanylmethyl)-4,5-dihydro-1,3-thiazol-2-ylamine, or a racemic mixture, an enantiomer or a diastereoisomer thereof or a mixture thereof, or a tautomer thereof or a pharmaceutically acceptable salt thereof.

14. The compound of formula (I) according to claim 12, which is chosen from the following:

(4RS)-4-(3-bromophenyl)-4,5-dihydro-1,3-thiazol-2-ylamine, 4-(4-methoxyphenyl)-4,5-dihydro-1,3-thiazol-2-ylamine, (−)-(4R)-4-(4-methoxyphenyl)-4,5-dihydro-1,3-thiazol-2-ylamine, or a tautomer thereof or a pharmaceutically acceptable salts thereof.

15. A process for preparing a compound of formula (I):

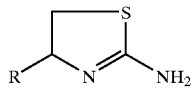

(I)

comprising the step of cyclizing a compound of formula (II) under suitable acidic reaction conditions such that said compound of formula (II) cyclizes to form said compound of formula (I):

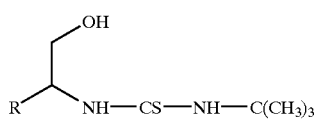

(II)

wherein R represents an -alk-S-alk-Ar radical, a phenyl radical or a phenyl radical substituted with one or more substituents of $C_{1-6}$alkoxy or halogen, and wherein Ar represents a phenyl radical and alk represents an $C_{1-6}$alkylene radical, and isolating the product.

16. A process for preparing a compound of formula (I):

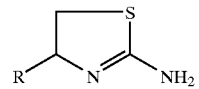

(I)

comprising the step of reacting a compound of formula (III):

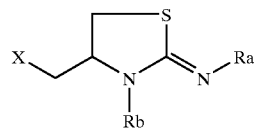

(III)

with a compound of formula HS-alk-Ar; wherein Rt is —CH$_2$—S-alk-Ar, Ar represents a phenyl radical and alk represents an $C_{1-6}$alkylene radical, X is halogen or a tosyl radical and Ra and Rb are hydrogen atoms or protecting groups for the amine function, and optionally, deprotecting the amine function and isolating the product.

17. A method of treating an illness which involves an abnormal production of nitric oxide (NO) by inducing an inducible NO-synthase (NOS-2)comprising administering to a patient in need thereof a therapeutically effective amount of a compound of formula (I):

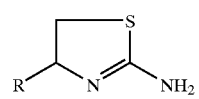

(I)

wherein R represents an -alk-S-alk-Ar radical, a phenyl radical or a phenyl radical substituted with one or more substituents of $C_{1-6}$alkoxy or halogen, and wherein Ar represents a phenyl radical and alk represents an $C_{1-6}$alkylene radical, or a racemic mixture, an enantiomer or a diastereoisomer thereof or mixtures thereof, or tautomer thereof or a pharmaceutically acceptable salt thereof, optionally in combination with a pharmaceutically acceptable carrier.

18. The method according to claim 17, wherein the illness is selected from the group consisting of multiple sclerosis, cerebral, focal or global ischemia, cerebral or spinal trauma, Parkinson's disease, Huntington's disease, Alzheimer's disease, amyotrophic lateral sclerosis, migraine, depression, schizophrenia, anxiety and epilepsy.

19. The method according to claim 17, wherein the illness is caused by inflammatory components.

20. The method according to claim 17, wherein the illness is caused by the growth of a tumor.

21. The process according to claim 15 wherein said process includes an additional step comprising converting said compound of formula (0 into a pharmaceutically acceptable salt by way of a reaction of said compound with a suitable inorganic or organic acid.

22. The process according to claim 16 wherein said process includes an additional step comprising converting said compound of formula (I) into a pharmaceutically acceptable salt by way of a reaction of said compound with a suitable inorganic or organic acid.

* * * * *